United States Patent [19]

Vanstraceele et al.

[11] Patent Number: 6,143,308
[45] Date of Patent: Nov. 7, 2000

[54] GELLED COMPOSITION OF ELASTOMERIC ORGANOPOLYSILOXANE COMBINED WITH A FATTY PHASE, FOR REMOVING MAKE-UP FROM AROUND THE EYES

[75] Inventors: Anne Vanstraceele, Paris; Catherine Marion, Sceaux, both of France

[73] Assignee: L'Oreal, Paris, France

[21] Appl. No.: 08/996,252

[22] Filed: Dec. 22, 1997

[30] Foreign Application Priority Data

Dec. 24, 1996 [FR] France .................................. 96 15982

[51] Int. Cl.$^7$ ...................................... A61K 7/48
[52] U.S. Cl. ........................ 424/401; 424/78.02; 514/63; 514/844
[58] Field of Search ................................ 424/401, 78.02; 514/844, 63

[56] References Cited

U.S. PATENT DOCUMENTS

| | | | |
|---|---|---|---|
| 5,165,917 | 11/1992 | Zabatto et al. ............................. | 424/70 |
| 5,217,641 | 6/1993 | Herstein .................................... | 252/171 |
| 5,266,321 | 11/1993 | Shukuzaki et al. ..................... | 424/401 |
| 5,525,344 | 6/1996 | Wivell . | |

FOREIGN PATENT DOCUMENTS 0 739 619 A1  10/1996  European Pat. Off. .

OTHER PUBLICATIONS

Masayuki Naganuma et al., "Makeup Cosmetics Containing Powdered Organopolysiloxane Elastomers, Nonporous Spherical Silica, and Oils", Chemical Abstracts, vol. 124, No. 4, Abstract No. 37392, Jan. 22,1996.

Akihiro Kuroda et al., "Sunscreens Containing Metal Oxides, Polyoxyalklene–Polysiloxanes, and Elastomers or Resin Waxes", Chemical Abstracts, vol. 126, No. 8, Abstract No. 108664, Feb. 24, 1997.

Charles M. Hansen, "The Three Dimensional Solubility Parameter—Key to Paint Component Affinities: I. Solvents, Plasticizers, Polymers, and Resins", Journal of Paint Technology, vol. 39, No. 505, pp. 104–113, Feb. 1967.

Allan F. M. Barton, Ph.D., CRC Handbook of Solubility Parameters and other Cohesion Parameters, CRC Press, Inc., pp. 153–161, 1983.

*Primary Examiner*—Jyothsan Venkat
*Attorney, Agent, or Firm*—Oblon, Spivak, McClelland, Maier & Neustadt, P.C.

[57] ABSTRACT

The invention relates to a cosmetic or dermatological composition gelled by an elastomeric organopolysiloxane which is at least partially crosslinked, combined with a fatty phase comprising at least one make-up-removing oil which is compatible with the organopolysiloxane, chosen from isohexadecane and isododecane, for removing make-up from around the eyes, more especially sensitive eyes, and containing little or no preserving agent or surfactant. The fatty phase in particular has average Hansen solubility parameters dD, dP and dH which satisfy the following three conditions:

(1) $dD \leq 20 \ (J/cm^3)^{1/2}$
(2) $dP \leq 10 \ (J/cm^3)^{1/2}$
(3) $dH \leq 15 \ (J/cm^3)^{1/2}$.

22 Claims, No Drawings

GELLED COMPOSITION OF ELASTOMERIC ORGANOPOLYSILOXANE COMBINED WITH A FATTY PHASE, FOR REMOVING MAKE-UP FROM AROUND THE EYES

BACKGROUND OF THE INVENTION

1. Field of the Invention

The present invention relates to a composition gelled by an organopolysiloxane, for removing make-up from around the eyes. This composition has a high level of tolerance, making it particularly suitable for removing make-up from around sensitive eyes. The invention applies both to the cosmetic and dermatological fields.

2. Discussion of the Background

The compositions for removing make-up from around the eyes which are conventionally used are generally in the form of a lotion or a milk. In addition, they contain preserving agents in order to provide microbiological protection and to prevent the growth of microorganisms. Microbial contamination of a composition is caused by the user when the product is taken up on his or her fingers. Furthermore, conventional make-up removers contain surfactants and oils which allow the removal of make-up.

Although very effective, these known compositions have a certain number of drawbacks. In particular, they are often difficult to take up and can run between the fingers. Moreover, they leave an uncomfortable and annoying residue or film on the eyes and/or the eyelids. Furthermore, the presence of preserving agents and/or surfactants can cause irritation of the eyes and/or the eyelids, which may result in redness, itching and stinging.

Skin cleansing compositions containing organopolysiloxane particles which ensure the removal of dirt and dead cells from the skin by a mechanical action (scrub) are known from document EP-A-295,886 to Dow Corning. However, these particles are not used to form a gelled composition of homogeneous appearance. In addition, the presence of these large-sized particles (larger than 3 $\mu$m) makes these compositions unusable for removing make-up from around the eyes and particularly from around sensitive eyes. Lastly, compositions described in that document contain surfactants, and are thus not suitable for removing make-up from around sensitive eyes.

In view of the aforementioned deficiencies attendant with the prior art compositions for removing make-up, it is clear that there exists a need in the art for a composition for removal of make-up which is suitable for use on senstive eyes, and contains little or no preserving agent or surfactant.

SUMMARY OF THE INVENTION

Applicants have discovered, surprisingly, that the combination of a solid, elastomeric, at least partially crosslinked organopolysiloxane with a fatty phase containing one or more specific make-up-removing cosmetic oil is capable of effectively removing make-up from around the eyes while at the same time, overcoming the above drawbacks. In particular, compositions containing this combination do not cause any annoyance or sensation of a film or discomfort on the eyes and/or the eyelids, after the removal of make-up.

Accordingly, one object of this invention is to provide a novel cosmetic or dermatological composition for removing make-up from around the eyes, which contains a physiologically acceptable medium gelled with (a) at least one solid, elastomeric, at least partially crosslinked organopolysiloxane combined with (b) a fatty phase which contains at least one make-up-removing oil chosen among isohexadecane and isododecane or a mixture of oils containing at least one make-up-removing oil chosen among isohexadecane and isododecane, wherein the mixture has average Hansen solubility parameters dD, dP and dH at 25° C. which satisfy the following three conditions:

(1) $dD \leq 20$ $(J/cm^3)^{1/2}$
(2) $dP \leq 10$ $(J/cm^3)^{1/2}$
(3) $dH \leq 15$ $(J/cm^3)^{1/2}$.

Another object of the invention is to provide a method for the preparation of a composition and/or in a composition for removing make-up from around the eyes, of a solid, elastomeric, at least partially crosslinked organopolysiloxane combined with a fatty phase comprising at least one make-up-removing oil chosen among isohexadecane and isododecane or a mixture of oils comprising at least one make-up-removing oil chosen among isohexadecane and isododecane, wherein the mixture has average Hansen solubility parameters dD, dP and dH at 25° C. which satisfy the following three conditions:

(1) $dD \leq 20$ $(J/cm^3)^{1/2}$
(2) $dP \leq 10$ $(J/cm^3)^{1/2}$
(3) $dH \leq 15$ $(J/cm^3)^{1/2}$.

The invention also relates to a process for removing make-up from around the eyes, whereby an effective amount of the above-described is applied to the eyes. With the foregoing and other objects, advantages and features of the invention that will become hereinafter apparent, the nature of the invention may be more clearly understood by reference to the following detailed description of the invention and to the appended claims.

DETAILED DESCRIPTION

More specifically, the subject of the invention is a cosmetic or dermatological composition for removing make-up from around the eyes, comprising a physiologically acceptable medium gelled with at least one solid, elastomeric, at least partially crosslinked organopolysiloxane combined with a fatty phase comprising at least one make-up-removing oil chosen from isohexadecane and isododecane or a mixture of oils including at least one make-up-removing oil chosen from isohexadecane and isododecane, wherein the mixture has average Hansen solubility parameters dD, dP and dH at 25° C. which satisfy the following three conditions:

(1) $dD \leq 20$ $(J/cm^3)^{1/2}$
(2) $dP \leq 10$ $(J/cm^3)^{1/2}$
(3) $dH \leq 15$ $(J/cm^3)^{1/2}$.

The expression "make-up-removing oil" is understood to refer to any physiologically acceptable fatty substance which is liquid at room temperature and is capable of dissolving the polymer(s), the resin(s), the wax(es), the dye(s) and/or the plasticizer(s) placed on the eyelashes, the eyebrows and/or the eyelids.

The term "elastomeric" is understood to refer to a supple, deformable material having viscoelastic properties and, in particular, the consistency of a sponge or a supple sphere.

The term "physiologically acceptable" is understood to mean compatible with human skin, eyes and keratin fibres.

The compositions are entirely suitable for sensitive eyes, that is to say for individuals who experience burning, heating, stinging, tingling, discomfort or tautness around the eyes, resulting from the use of certain cosmetics, rapid changes in temperature, exposure to UV radiation, to dusts or to air currents.

The definition of oils in the three-dimensional solubility space according to Hansen is described in the article by C. M. Hansen: "The three dimensional solubility parameters" J. Paint Technol. 39, 105 (1967). This space is defined by the parameters dD, dP, dH; they are expressed in $(J/cm^3)^{1/2}$:

dD characterizes the London dispersion forces derived from the formation of dipoles induced during molecular impacts;

dP characterizes the Debye interaction forces between permanent dipoles and the Keesom interaction forces between induced dipoles and permanent dipoles;

dH characterizes the specific forces of interaction (of the hydrogen bonding, acid/base, donor/acceptor, etc. type).

The organopolysiloxanes in the composition of the invention have a noteworthy power for gelling oil. They do not cause the skin around the eyes to dry out and they provide good cosmetic properties. These novel elastomers lead to compositions that are comfortable when applied, soft, non-sticky and pleasant to the touch. This softness is due, on the one hand, to the texture of the organopolysiloxanes and, on the other hand, to their properties which are comparable with those of microsponges that trap the oils, in particular the make-up-removing oils, in the composition.

The organopolysiloxanes in the composition according to the invention are partially or totally crosslinked and of three-dimensional structure. When included in a fatty phase as defined above, they become converted, depending on the level of fatty phase used, from a product of spongy appearance when they are used in the presence of low contents of fatty phase, into a homogeneous gel in the presence of larger amounts of fatty phase.

The compositions of the invention are in the form of a relatively fluid gel or a paste of homogeneous appearance. This type of presentation affords a certain number of advantages, such as ease of uptake of the product, without significant loss, ease of application and precise dosage of the amount of product needed for removing the make-up from around the eyes.

The organopolysiloxanes in the composition according to the invention can be chosen from those described in the documents EP-A-383,540 and EP-A-545,002 or patent U.S. Pat. No. 5,266,321, which are hereby incorporated by reference in their entireties. According to the aforementioned U.S. patent, the organopolysiloxanes are chosen in particular from:

i) organopolysiloxanes comprising units $R_2SiO$ and $RSiO_{1.5}$ and optionally units $R_3SiO_{0.5}$ and/or $SiO_2$ in which the radicals R, independently of each other, denote a hydrogen, an alkyl such as methyl, ethyl or propyl, an aryl such as phenyl or tolyl, an unsaturated aliphatic group such as vinyl, and in which the weight ratio of the units $R_2SiO$ to the units $RSiO_{1.5}$ ranges from 1/1 to 30/1;

ii) organopolysiloxanes which are insoluble and swellable in a silicone oil, obtained by addition of an organohydrogenopolysiloxane (1) and of an organopolysiloxane (2) having unsaturated aliphatic groups, such that the amount of hydrogen or of unsaturated aliphatic groups in (1) and (2) respectively is between 1 and 20 mol % when the organopolysiloxane is non-cyclic and between 1 and 50 mol % when the organopolysiloxane is cyclic.

The organopolysiloxanes in the composition of the invention are, for example, those sold under the names KSG6 from Shin-Etsu, Gransil from Grant Industries (SR-CYC, SR DMF10, SR-DC556), or those sold in the form of preconstituted gels (KSG15, KSG17, KSG16, KSG18 and KSG20 from Shin-Etsu, Gransil SR 5CYC gel, Gransil SR DMF 10 gel, Gransil SR DC556 gel, SF 1204 and JK 113 from General Electric. A mixture of these commercial products can also be used.

According to the invention, when they are present in powder form, before incorporation of the oils, the elastomeric organopolysiloxanes have a particle size of not more than 1 $\mu$m, which may be as low as 0.5 $\mu$m.

Preferably, the elastomeric organopolysiloxane(s) is/are present in the composition in an active material concentration ranging from 0.1% to 30% and more preferably from 3% to 25% of the total weight of the composition.

The fatty phase which allows the elastomeric organopolysiloxane of the invention to swell comprises at least one or more cosmetic oils capable of removing make-up from around the eyes, chosen from isohexadecane and isododecane, or a mixture of oils comprising these make-up-removing oils, the mixture having average solubility parameters dD, dP and dH at 25° C., according to the Hansen solubility space, which satisfy the following conditions:

(a) $dD \leq 20$ $(J/cm^3)^{1/2}$ and preferably $10 \leq dD \leq 19$ $(J/cm^3)^{1/2}$ (b) $dP \leq 10$ $(J/cm^3)^{1/2}$ and preferably $dP \leq 7$ $(J/cm^3)^{1/2}$ (c) $dH \leq 15$ $(J/cm^3)^{1/2}$ and preferably $dH \leq 13$ $(J/cm^3)^{1/2}$ and even more preferably $dH \leq 8$ $(J/cm^3)^{1/2}$.

Preferably, the fatty phase includes, in addition to isohexadecane and/or isododecane, one or more make-up-removing oils which satisfies each of the solubility conditions defined above. These oils are chosen in particular from:

linear or branched hydrocarbons of mineral or synthetic origin, such as liquid petroleum jelly, squalane and equivalents;

short-chain (less than 12 carbon atoms) fatty acid esters such as octyldodecyl neopentanoate; or mixtures thereof.

The compositions of the invention have a high make-up-removing power without the need for surfactants. Thus, advantageously, they are free of surfactants, which gives them a high level of tolerance, and they can be used several times a day, if necessary, even by individuals with sensitive eyes. In addition, they make it possible to remove make-up compositions (mascara, eyeliner, pencil, face powder, concealer stick), which are resistant to water, to sebum and/or to transfer onto a support other than the skin and keratin fibres, from around the eyes.

The term "free of surfactant" should be understood to mean less than 1% by weight of surfactant, preferably no surfactant at all.

Preferably, the fatty phase is present in the composition in a concentration ranging from 5% to 90% and more preferably from 20% to 80% of the total weight of the composition. In particular, on account of this high level of fatty phase, it is possible to obtain an anhydrous composition. This type of composition has the advantage, over compositions containing a large amount of water (more than 10%), of not needing preserving agents since the larger the amount of water, the more the medium promotes the growth of microorganisms. Thus, the composition of the invention is advantageously free of preserving agents, that is to say that it contains less than 1% by weight of preserving agent and better still no preserving agent at all.

Advantageously, the make-up-removing oils participating in the swelling of the organopolysiloxane represent from 10% to 90% and preferably from 30% to 60% of the total weight of the composition.

In addition to the above make-up-removing oils, the fatty phase in accordance with the invention can contain an oily phase containing oils conventionally used in the cosmetic or dermatological field, known as complementary oils, which may or may not remove make-up from around the eyes and which, when taken as they are, do not satisfy the Hansen solubility conditions defined above. In accordance with the invention, these fatty phases must be mixed with suitable make-up-removing oils as defined above such that the total mixture of oils (make-up-removing+non-make-up-removing oils) satisfies the conditions of the Hansen solubility parameters defined above.

Examples of make-up-removing oils which does not satisfy the above conditions, are long-chain (longer than 12 carbon atoms) fatty acid esters such as octyl or isopropyl palmitate or myristate.

The oily phase can thus contain one or more complementary non-make-up-removing oils chosen in particular from:

silicone oils of low viscosity (preferably less than 100 cst at 25° C.) such as linear or branched polysiloxanes with a low degree of polymerization, such as methylpolysiloxane, methylphenylpolysiloxane, ethylmethylpolysiloxane, ethylphenylpolysiloxane, hydroxymethylpolysiloxane, alkylpolydimethylsiloxane and cyclic polysiloxanes such as octamethylcyclopentasiloxane, decamethylcyclopentasiloxane or mixtures thereof: these silicone oils have the advantage of improving the feel, of participating in the swelling of the elastomeric organopolysiloxane and of satisfying the above solubility conditions;

plant oils such as liquid triglycerides, for example sunflower oil, corn oil, soybean oil, marrow oil, grapeseed oil, sesame oil, hazelnut oil, apricot oil, macadamia oil, castor oil and caprylic/capric acid triglycerides such as those sold under the names Miglyol 810, 812 and 818 by the company Dynamit Nobel.

These non-make-up-removing oils are preferably used in concentrations ranging from 0 to 50% and more preferably from 0 to 40% of the total weight of the composition.

The gelled composition resulting from the combination of the above oils and the organopolysiloxane can be used as it is and can itself constitute a composition for removing make-up from around the eyes. It can also be incorporated into a more complex formulation for removing make-up from around the eyes, in an amount which is effective for obtaining both the desired texture and the desired viscosity and good removal of make-up from around the eyes.

The composition according to the invention can also contain additives conventionally used in the art, which have no irritant or intolerance side effects on the eyes, such as moisturizers and emollients. These additives are present in amounts preferably ranging from 0 to 10% of the total weight of the composition.

The invention also relates to a cosmetic process for removing make-up from around the eyes, wherein an effective amount of a composition as defined above is applied to the eyes.

The invention also relates to the use of at least one elastomeric, solid, at least partially crosslinked organopolysiloxane combined with a fatty phase comprising at least one make-up-removing oil chosen among isohexadecane and isododecane or a mixture of oils comprising at least one make-up-removing oil chosen among isohexadecane and isododecane, the said mixture having average Hansen solubility parameters dD, dP and dH at 25° C. which satisfy the following three conditions:

(1) $dD \leq 20$ $(J/cm^3)^{1/2}$
(2) $dP \leq 10$ $(J/cm^3)^{1/2}$
(3) $dH \leq 15$ $(J/cm^3)^{1/2}$.

in, and/or for the preparation of a cosmetic or dermatological composition for removing make-up from around the eyes.

Having generally described this invention, a further understanding can be obtained by reference to certain specific examples which are provided herein for purposes of illustration only and are not intended to be limiting unless otherwise specified. The percentages are given by weight.

EXAMPLES

Example 1

Preparation of a Fluid Gel for Removing Make-up from Around the Eyes

| | |
|---|---|
| Partially crosslinked mixture of 40% by weight polydimethylsiloxane oil 6 cst and 60% by weight polydimethyl-organosiloxane, sold under the name KSG 6 by Shin Etsu | 25% |
| Isododecane | 50% |
| Cyclomethicone | 25% |

A fluid gel which is easy to spread and which gives the eyes, after removal of make-up and cleansing with cotton wool, a soft feel for the skin around the eyes, is obtained.

Example 2

Preparation of a Gel for Removing Make-up from Around the Eyes

| | |
|---|---|
| Partially crosslinked mixture of 40% by weight polydimethylsiloxane oil 6 cst and 60% by weight polydimethyl-organosiloxane, sold under the name KSG 6 by Shin Etsu | 40% |
| Isododecane | 60% |

A gel which is easy to spread and which gives the eyes, after removal of make-up and cleansing with cotton wool, a soft feel with no sensation of a film, is obtained.

Example 3

In vivo Tests of Compositions

The efficacy and the level of comfort of compositions 1 and 2 above were evaluated in a first test in vivo on a panel of 10 individuals with sensitive skin and sensitive eyes, made up with a waterproof mascara.

The make-up-removing power and the level of comfort proved to be particularly good: most of the women considered the removal of make-up to be entirely satisfactory.

A second test on 46 individuals, 72% of whom have sensitive eyes, gave very good results with composition 2. Thus, 82% of the women note a good, or even a very good, make-up-removing power for the eyes which is greater than (54%) or equal to (20%) that of their usual product. The level of eye comfort is, except for two cases for stinging and/or redness of the eyes, satisfactory during and after the application.

As regards the cosmetic appearance, the texture and the content of fatty substances are preferred by 82% of the women, and this product was unanimously found to be soft when applied. 80% of the women said their eyelids were soft after removal of the make-up.

In conclusion, 76% of the women on the panel declared this product to be satisfactory, mainly on account of its good make-up-removing power.

This application is based on French application 96-15982, filed Dec. 24, 1996, which is incorporated by reference herein in its entirety.

Having now fully described the invention, it will be apparent to one of ordinary skill in the art that many changes and modifications can be made thereto without departing from the spirit or scope of the invention as set forth herein.

What is claimed as new and is desired to be secured by Letters Patent of the United States is:

1. An anhydrous cosmetic or dermatological composition for removing make-up from around the eyes, comprising a physiologically acceptable medium gelled with
    (a) at least one solid, elastomeric, at least partially crosslinked organopolysiloxane selected from the group consisting of:
        i) polyorganopolysiloxanes comprising units $R_2SiO$ and $RSiO_{1.5}$ and optionally units $R_3SiO_{0.5}$, $SiO_2$ or both $R_3SiO_{0.5}$ and $SiO_2$, in which the radicals R, independently of each other, denote a hydrogen, an alkyl group an aryl group or an unsaturated aliphatic group, and in which the weight ratio of the units $R_2SiO$ to the units $RSiO_{1.5}$ ranges from 1/1 to 30/1; and
        ii) organopolysiloxanes obtained by addition of an organohydrogenopolysiloxane (1) and of an organopolysiloxane (2) having unsaturated aliphatic groups, such that the amount of hydrogen or of unsaturated aliphatic groups in (1) and (2) respectively is between 1 and 20 mol % when the organopolysiloxane is non-cyclic and between 1 and 50 mol % when the organopolysiloxane is cyclic, combined with
    (b) a fatty phase comprising at least one make-up-removing oil selected from the group consisting of isohexadecane, isododecane and a mixture thereof, said mixture having average Hansen solubility parameters dD, dP and dH at 25° C. which satisfy the following three conditions:
        (1) $dD \leq 20$ $(J/cm^3)^{1/2}$
        (2) $dP \leq 10$ $(J/cm^3)^{1/2}$
        (3) $dH \leq 15$ $(J/cm^3)^{1/2}$.

2. The composition according to claim 1 wherein the medium is free of surfactant, preserving agent or both surfactant and preserving agent.

3. The composition according to claim 1, wherein the fatty phase comprises a mixture of isohexadecane and isododecane, said mixture having average Hansen solubility parameters dD, dP and dH at 25° C. which satisfy the following three conditions:
    (a) $10 \leq dD \leq 19$ $(J/cm^3)^{1/2}$
    (b) $dP \leq 7$ $(J/cm^3)^{1/2}$
    (c) $dH \leq 13$ $(J/cm^3)^{1/2}$.

4. The composition according to claim 1, wherein the make-up-removing oil comprises an additional oil which satisfies said conditions and is selected from the group consisting of:
    linear or branched hydrocarbons of mineral or synthetic origin;
    short-chain fatty acid esters; and
    mixtures thereof.

5. The composition according to claim 1, wherein the fatty phase also contains at least one complementary make-up-removing or non-make-up-removing oil which by itself does not satisfy said conditions, but which upon mixture with the make-up-removing oil does satisfy said conditions.

6. The composition according to claim 5, wherein the complementary oil is selected from the group consisting of:
    linear or branched polysiloxanes, alkylpolydimethylsiloxanes and cyclic polysiloxanes;
    plant oils containing triglycerides;
    long-chain fatty acid esters; and
    mixtures thereof.

7. The composition according to claim 1, wherein the fatty phase represents from 5% to 90% of the total weight of the composition.

8. The composition according to claim 1, wherein the organopolysiloxane is present at an active material concentration ranging from 0.1 to 30% of the total weight of the composition.

9. The composition according to claim 8, wherein the organopolysiloxane is present at an active material concentration ranging from 3 to 25% of the total weight of the composition.

10. The composition according to claim 1, wherein the organopolysiloxane is in the form of a powder before it is introduced into the composition, and has a particle size of not more than 1 μm.

11. A method for the preparation of an anhydrous composition for removing make-up from around the eyes, comprising combining
    a) a solid, elastomeric, at least partially crosslinked organopolysiloxane selected from the group consisting of:
        i) polyorganopolysiloxanes comprising units $R_2SiO$ and $RSiO_{1.5}$ and optionally units $R_3SiO_{0.5}$, $SiO_2$ or both $R_3SiO_{0.5}$ and $SiO_2$, in which the radicals R, independently of each other, denote a hydrogen, an alkyl group an aryl group or an unsaturated aliphatic group, and in which the weight ratio of the units $R_2SiO$ to the units $RSiO_{1.5}$ ranges from 1/1 to 30/1; and
        ii) organopolysiloxanes obtained by addition of an organohydrogenopolysiloxane (1) and of an organopolysiloxane (2) having unsaturated aliphatic groups, such that the amount of hydrogen or of unsaturated aliphatic groups in (1) and (2) respectively is between 1 and 20 mol % when the organopolysiloxane is non-cyclic and between 1 and 50 mol % when the organopolysiloxane is cyclic, with
    b) a fatty phase comprising at least one make-up-removing oil selected from the group consisting of:
        i) isohexadecane;
        ii) isododecane; and
        iii) a mixture of isohexadecane and isododecane,
    such that said mixture has average Hansen solubility parameters dD, dP and dH at 25° C. which satisfy the following three conditions:
        (1) $dD \leq 20$ $(J/cm^3)^{1/2}$
        (2) $dP \leq 10$ $(J/cm^3)^{1/2}$
        (3) $dH \leq 15$ $(J/cm^3)^{1/2}$.

12. The method according to claim 11, wherein the composition is in the form of a gel.

13. The method according to claim 11, wherein the composition is in anhydrous form.

14. The method according to claim 11, wherein the make-up-removing oil or the mixture of oils having average Hansen solubility parameters dD, dP and dH at 25° C. satisfy the following three conditions:

(a) $10 \leq dD \leq 19$ $(J/cm^3)^{1/2}$ (b) $dP \leq 7$ $(J/cm^3)^{1/2}$ (c) $dH \leq 13$ $(J/cm^3)^{1/2}$.

15. The method according to claim 11, wherein the fatty phase further comprises at least one make-up-removing oil selected from the group consisting of:

linear or branched hydrocarbons of mineral or synthetic origin;

short-chain fatty acid esters; and mixtures thereof.

16. The method of claim 11, wherein the composition is free of surfactant, preserving agent or both surfactant and preserving agent.

17. The method of claim 11, wherein the fatty phase also contains at least one complementary make-up-removing or non-make-up-removing oil which by itself does not satisfy the conditions, but whose mixture with the make-up-removing oil does satisfy said conditions.

18. The method according to claim 17, wherein the complementary oil is selected from the group consisting of:

linear or branched polysiloxanes, alkylpolydimethylsiloxanes and cyclic polysiloxanes;

plant oils containing triglycerides;

long-chain fatty acid esters; and mixtures thereof.

19. The method according to claim 11, wherein the fatty phase represents from 5 to 90% of the total weight of the composition.

20. The method according to claim 11, wherein the organopolysiloxane is present in an active material concentration ranging from 0.1 to 30% of the total weight of the composition.

21. The method according to claim 20, wherein the organopolysiloxane is present in an active material concentration ranging from 3 to 25% of the total weight of the composition.

22. A process for removing make-up from around the eyes, comprising applying to the eyes a make-up removal effective amount of a composition as defined in claim 1.

* * * * *